(12) United States Patent
Klein

(10) Patent No.: US 7,556,037 B2
(45) Date of Patent: Jul. 7, 2009

(54) INHALATION AID

(76) Inventor: Christoph Klein, Randersbergweg 532, Großgmain-Hinterreit (AT) 5084

( * ) Notice: Subject to any disclaimer, the term of this patent is extended or adjusted under 35 U.S.C. 154(b) by 446 days.

(21) Appl. No.: 11/225,844

(22) Filed: Sep. 9, 2005

(65) Prior Publication Data

US 2006/0000471 A1 Jan. 5, 2006

Related U.S. Application Data

(63) Continuation of application No. PCT/AT02/00051, filed on Feb. 14, 2002.

(51) Int. Cl.
*A61M 15/08* (2006.01)
(52) U.S. Cl. .............. 128/203.23; 128/200.14; 128/200.23; 128/203.15; 128/203.24
(58) Field of Classification Search .......... 128/200.14, 128/200.23, 203.15, 203.23, 203.24
See application file for complete search history.

(56) References Cited

U.S. PATENT DOCUMENTS

| 3,994,421 | A | 11/1976 | Hansen ..................... 222/182 |
| 4,509,515 | A | 4/1985 | Altounyan et al. .......... 128/200 |
| 5,571,246 | A | 11/1996 | Alldredge .................. 128/200 |
| 5,809,996 | A | * | 9/1998 | Alldredge .............. 128/200.23 |
| 6,510,818 | B2 | * | 1/2003 | Barney et al. ............... 119/831 |

FOREIGN PATENT DOCUMENTS

| DE | 3229702 A1 | 3/1983 |
| DE | 3816276 A1 | 11/1990 |
| DE | 19941236 A1 | 3/2001 |
| EP | 0009667 A1 | 4/1980 |
| EP | 0384050 A1 | 8/1990 |
| EP | 0385212 A2 | 9/1990 |
| GB | 2110543 A | 6/1983 |
| GB | 2182249 A | 5/1987 |
| GB | 2301040 A | 11/1995 |
| WO | WO96/37249 | 11/1996 |
| WO | WO97/12638 | 4/1997 |
| WO | WO00/33902 | 6/2000 |
| WO | WO01/87396 | 11/2001 |

* cited by examiner

*Primary Examiner*—Michael Brown
*Assistant Examiner*—Nihir Patel

(57) ABSTRACT

An inhalation aid to be used in connection with an aerosol dispenser. The inhalation aid includes a chamber designed with an opening for connection to an aerosol dispenser and an opening including a mouthpiece for drawing the aerosol. The chamber is designed with a variable volume. The chamber is delimited by a conically tapering expansion bellows made of a continuous, elastic material, whereby a simple and tight construction of the inhalation aid is obtainable.

15 Claims, 3 Drawing Sheets

INHALATION AID

This is a continuation of PCT/AT02/00051 filed Feb. 14, 2002 and published in German.

FIELD OF THE INVENTION

The present invention relates to an inhalation aid for use in connection with an aerosol dispenser, comprising a chamber designed with an opening for connection to an aerosol dispenser and an opening including a mouthpiece for drawing the aerosol, said chamber being designed with a variable volume.

PRIOR ART

Dosing aerosols are widely used forms of administration of drugs for treating bronchial asthma and chronic bronchitis. Even with allergies, dosing aerosols have been employed to an increasing extent. The inhalative treatment of such diseases with dosing aerosols has proven to be highly effective especially with acutely occurring symptoms such as dyspnoea. A dosing aerosol is usually contained in a drug container which comprises the individual components, namely the micronized active substance, a suspending agent and a propellant. The individual components are mixed by shaking prior to application. After every spray pulse, these components will be newly supplied to the dosing chamber of the drug container in standardized amounts, if the drug container is held vertically, and only the amount contained in the dosing chamber will be ejected at a spray pulse.

In order to be able to inhale propellant-containing dosing aerosols, predominantly L-shaped aerosol dispensers are used, as can be taken, for instance, from U.S. Pat. No. 3,994,421, U.S. Pat. No. 4,509,515, DE-32 29 702 or DE-38 16 276. L-shaped aerosol dispensers involve the big disadvantage of the aerosol emerging from the mouthpiece of the dispenser in an uncontrolled manner and at a very high speed, thus causing the major portion of the aerosol, mostly more than 80%, to remain adhering in the mouth, throat and jaw region at every spray pulse. Only about 6 to 20% of the aerosol reaches the respiratory tract, where its therapeutic effect will evolve. The high drug portion remaining in the mouth, throat and jaw region may cause unpleasant side-effects with various dosing aerosols, which may possibly require further treatment with additional drugs. With aerosol dispensers of that type, the mouth, throat and jaw region, thus, serves as a spray chamber.

All dosing aerosols are essentially identical in terms of functional structure. The suspension usually contained in the drug container comprises micronized particles of the active substance. In the case of conventional L-shaped aerosol dispensers, the micronized particles of the active substance are enveloped by so-called primary droplets when emerging from the nozzle. When leaving the nozzle, the primary droplets are normally so large as to be unable to float, thus acting like projectiles in the mouth, throat and jaw region. Based on the L-shaped aerosol dispensers, further special inhalation aids, so-called spacers, have, therefore, been offered to contribute to reducing drug deposits in the mouth, throat and jaw region, as has become known, for instance, from EP-A 0 009 667. Another configuration of an inhalation aid is to be taken from EP-A 0 384 050, wherein a cylinder that is not variable in volume terms is designed with a variable cross section on its inlet end and a valve on its outlet end.

Those inhalation aids are large-volume spray chambers into which the aerosol is to be at first sprayed by the L-shaped aerosol dispensers. To the primary droplets formed at a spray pulse, a sufficiently long path will, thus, be available to decelerate their high speed. Due to the large volume of the spacer, the primary droplets are, moreover, heated and hence able to evaporate. After evaporation, as many active-substance particles as possible, which are smaller than 5 μm and hence lung-accessible, are aimed to float within the spacer, with all non-floatable drug particles accumulating and remaining at the wall of the spacer.

If no such additional inhalation aid is used at the application of dosing aerosols by the aid of usual L-shaped aerosol dispensers, the primary droplets, due to their dimensions, will shoot into the mouth space like projectiles and for the major part remain adhering to the throat wall as described above, because no sufficiently long path and no sufficiently large volume are available for the primary droplets to evaporate and reduce their high speed.

When using a spacer or inhalation aid in combination with an aerosol dispenser, the mouth, throat and jaw deposits of the dosing aerosol caused so far, by contrast, will move into the spacer, thus nearly averting or largely reducing the risk of side-effects like thrush or inflammations. The drug deposit in the lung will increase only minimally. Another advantage of the spacer consists in that the floatable active-substance particles will remain within the spacer for some time because of the large volume of the latter, thus giving the user enough time to inhale the aerosol from the spacer. Furthermore, the coordination problem of the simultaneous release of an aerosol spray pulse and an inhalation has, thus, been solved. The spacer is a useful product to improve therapies with dosing aerosols, reduce subjective side-effects and solve said coordination problem.

The biggest problem faced when using an inhalation aid or spacer of this kind, however, resides in its large dimensions, and such spacers are, therefore, unsuitable as pocket devices and also cumbersome to use on account of their sizes. It is almost impossible for users to carry the spacers along with them all the time. The users of dosing aerosols, as a rule, have to use their dosing aerosols several times a day and would, in fact, be glad to have the spacer at their disposal as a useful aid.

Problems with large-volume inhalation aids are partially reduced by proposing spacers having variable volumes as can, for instance, be taken, from GB-A 2 110 543, GB-A 2 182 249, U.S. Pat. No. 5,074,294, WO 97/12638, U.S. Pat. No. 5,571 246, GB-A 2 301 040 or WO 96/37249. However, those known inhalation aids involve the disadvantage of constituting rather complex technical constructions calling for excessively large structural expenses and, hence, being not producible in a cost-effective manner.

From WO 97/12638, U.S. Pat. No. 5,571,246 and GB-A 2 301 040, embodiments have become known, in which, in order to obtain a pyramid-like or funnel-shaped form of the spacer or inhalation aid, a plurality of conically tapering rings mutually engaging, and fitted into each another in the telescoped state, are provided, which are displaceable relative to one another in the direction of the longitudinal axis of the inhalation aid. The known construction involves the disadvantage that no sufficient tightness is readily obtainable between the individual rings such that, on the one hand, a loss of the active substance or drug will have to be feared and, on the other hand, the penetration of possibly noxious particles from the external surroundings during the drug absorption procedure cannot be excluded.

Another problem arising in known inhalation aids consists in that every supplier of dosing aerosols, as a rule, offers their own spacers which are usable only with accordingly adapted, special aerosol dispensers and dosing aerosols. It is, thus, made almost impossible to the user to employ products of other manufacturers in connection with the existing spacer.

SUMMARY OF THE INVENTION

It is the object of the present invention, based on an inhalation aid or spacer of the initially defined kind, to further develop the same in a manner that, despite its simple construction, a reliable and, in particular, tight inhalation aid is made available, which can be brought into a transport position requiring reduced space and a position of use, in which an accordingly large volume of the chamber of the inhalation aid is provided.

To solve this object, the inhalation aid according to the invention, departing from an inhalation aid or spacer of the initially defined kind, is essentially characterized in that the chamber is delimited by a conically tapering expansion bellows made of a continuous, elastic material. Due to the fact that, according to the invention, the chamber of the inhalation aid or spacer is delimited by a conically tapering expansion bellows made of a continuous, elastic material, tightness problems as are to be feared with the prior art pointed out above will be excluded. In addition, such an elastic material may be comprised of a material resistant to the drugs or substances to be applied. It is, moreover, feasible to maintain the required hygienic conditions with such a continuous, elastic material. Furthermore, such an expansion bellows can be manufactured in a single manufacturing procedure using but one mould or tool and an accordingly uniform material. In this context, it is proposed according to a preferred embodiment that the expansion bellows is made of silicone. The use of silicone for the production of the expansion bellows not only renders feasible a simple and cost-effective production, but also enables the observance of the conditions and, in particular, hygienic and medico-technical conditions required for this purpose of use.

According to another preferred embodiment, it is proposed that the expansion bellows comprises at least one ring-shaped reinforcement having a material cross section increased relative to the adjacent portions of the expansion bellows. By such a ring-shaped reinforcement, or a plurality of ring-shaped reinforcements having accordingly differing diameters or clear widths, it is feasible, on the one hand, to obtain a suitable reinforcement of the expansion bellows to ensure the reliable assumption of a position of use while maintaining the desired chamber volume. On the other hand, at least one such ring-shaped reinforcement, or a plurality of matching ring-shaped reinforcements, allow for the selective folding or collapsing into a transport position requiring less space, wherein, by providing several ring-shaped reinforcements having diameters or clear widths reduced in accordance with the conical taper of the expansion bellows, these ring-shaped reinforcements in the folded state of the inhalation aid are each inserted into one another or mutually taken up by one another.

In order to obtain the desired simplified handling ability both when assuming the position of use and defining the necessary chamber volume and for changing into a transport position requiring little space, the configuration is preferably devised such that the outer surface of the expansion bellows is designed to be stepped or offset in the region of the end face(s) of the ring-shaped reinforcement(s) oriented towards the tapering end.

In order to support the folding procedure, it is provided according to another preferred embodiment that the expansion bellows is designed to have a reduced material cross section in its portion immediately following the reinforcement(s), particularly on the chamber side face oriented towards the interior. Such portions having reduced material cross sections allow for the simple folding of the chamber-defining expansion bellows, particularly when changing into the transport position, due to the bending lines defined by the reduced material cross sections.

In order to enable the protected reception of the chamber-defining expansion bellows in the transport position, it may be provided that the expansion bellows, in its folded state, is capable of being received in a pot-like, rigid housing which comprises the mouthpiece for drawing aerosol from the chamber, as in correspondence with another preferred embodiment of the inhalation aid according to the invention. Such a pot-like housing is able to receive or cover the expansion bellows in the folded state or transport position to the major extent so as to avoid damage to the expansion bellows during transportation.

In order to properly fix the expansion bellows to the housing comprising the mouthpiece, it is provided according to a further preferred embodiment that the expansion bellows, on its end having a larger cross section, is provided with a bead or flange to which a retaining ring is fixable, wherein it is further preferred in this context that the retaining ring is connectable and, in particular, detachably connectable with the housing provided to receive the expansion bellows. Such a combination with the housing, of a retaining ring capable of being fixed to the expansion bellows not only allows for the safe reception of the chamber-delimiting expansion bellows in the housing, but due to said detachable fixation also ensures that the expansion bellows and the interior of the chamber can be regularly and readily cleaned according to demands. For a simple and reliable fixation, it is proposed in this respect that the connection between the retaining ring and the housing is comprised of a screw connection or bayonet catch, as in correspondence with a further preferred embodiment of the inhalation aid according to the invention.

In order to ensure the proper mutual fixation of the individual elements of the inhalation aid according to the invention, it is, moreover, provided that markings, or snap-on or adjusting elements, are provided on the retaining ring and/or housing. Such markings, or snap-on or adjusting elements, enable the reliable and tight fixation of the individual parts to one another as well as the simple and reliable assembly after a separation of the individual parts, for instance, for cleaning purposes.

In order to provide an additional function of protection, particularly to the opening of the mouthpiece as well as the further opening provided for connection to an aerosol dispenser, it is, moreover, suggested that cover or closing means are provided for the openings of the chamber, as in correspondence with a further preferred embodiment of the inhalation aid according to the invention.

SHORT DESCRIPTION OF THE DRAWINGS

In the following, the invention will be explained in more detail by way of exemplary embodiments schematically illustrated in the attached drawing. Therein:

Figure 3:
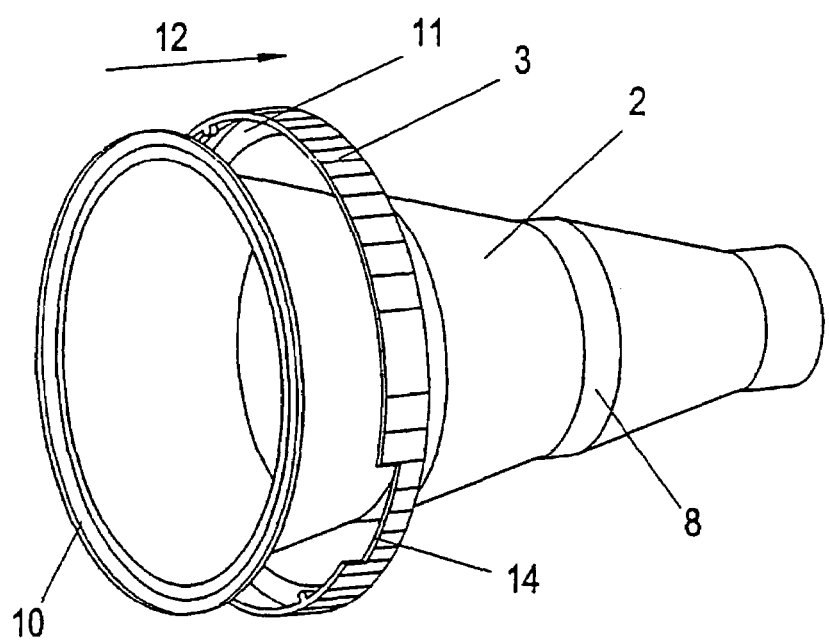
Figure 4:
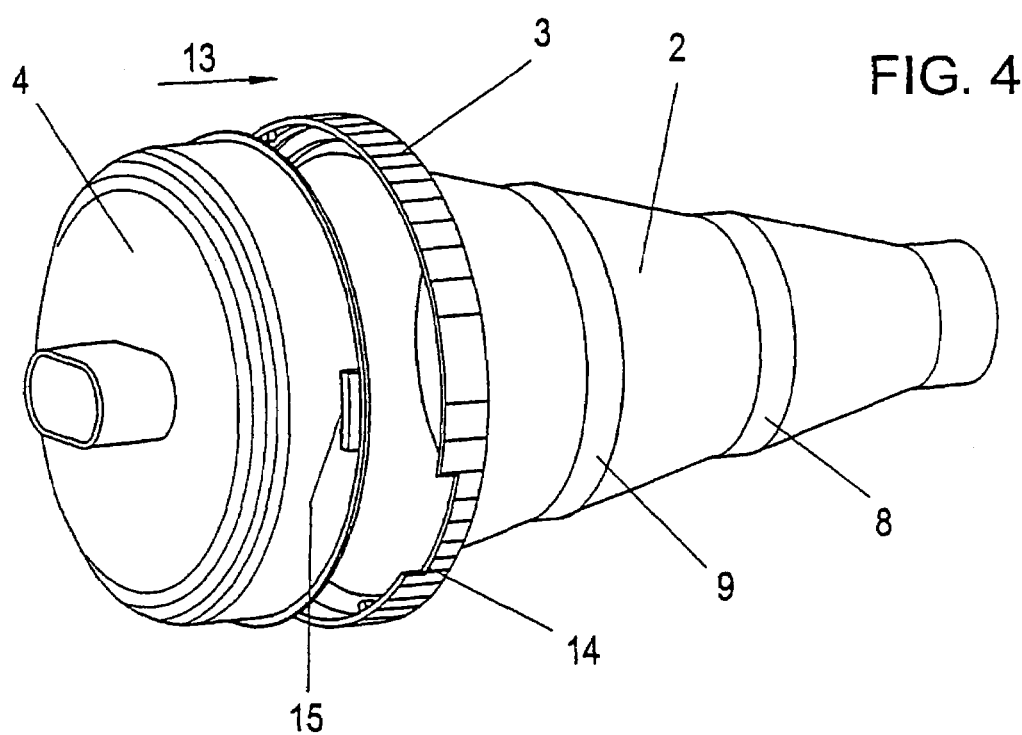
Figure 5:
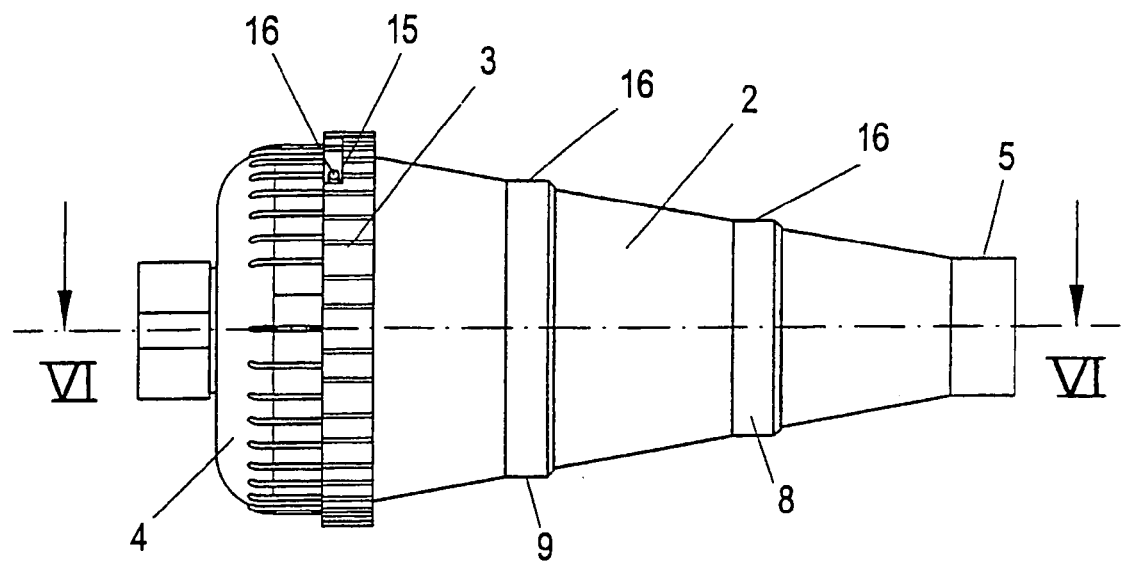
Figure 6:
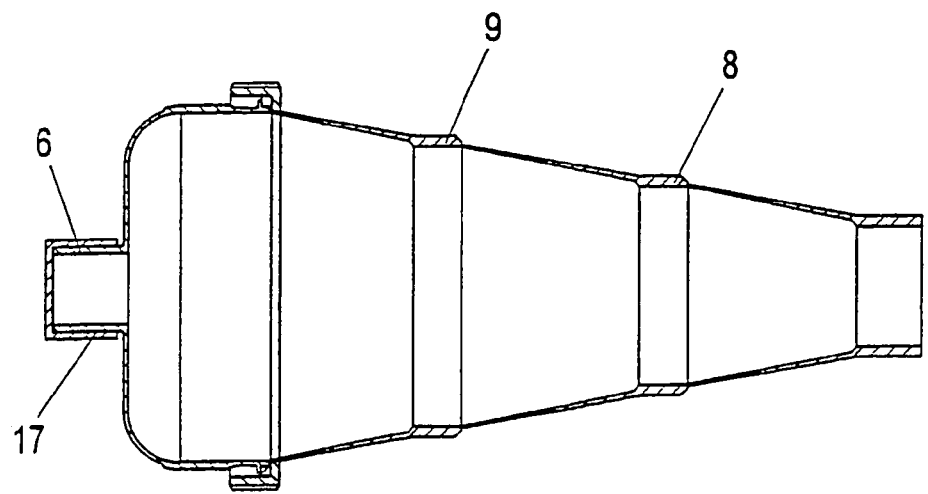

FIG. 3 in a perspective, exploded view shows the expansion bellows of the inhalation aid according to the invention with a partially loosened retaining ring;

FIG. 4 in an exploded view similar to that of FIG. 3 shows the inhalation aid according to the invention;

FIG. 5 is a schematic side view of the inhalation aid according to the invention in the operating position; and FIG. 6 is a sectional view along line VI-VI of FIG. 5 through the inhalation aid according to the invention.

DETAILED DESCRIPTION OF PREFERRED EMBODIMENTS

In the Figures, the inhalation aid 1 comprises a conically tapering expansion bellows 2 defining a chamber, to which expansion bellows a retaining ring 3 is fixable as will be explained in more detail below, said retaining ring 3 being detachably fixable to a pot-like, rigid housing 4 as well again be explained in more detail below. As is clearly apparent from a comparison of FIGS. 1 and 2, the conically tapering expansion bellows 2, which is made of a continuous, elastic material, defines a chamber of variable volume, wherein the expansion bellows 2, on its end having a smaller cross section, is designed to include an opening 5 for attachment to an aerosol dispenser not illustrated in detail. The inhalation aid 1 is, moreover, formed with an opening 6 defining or comprising a mouthpiece on the housing 4.

Alternatively to the illustrated embodiment comprising an expansion bellows separate from the retaining ring 3 and the housing 4, it is also feasible to provide a suitable one-piece embodiment, which again includes a mouthpiece-defining opening 6, on the end having a larger cross section.

Figure 1:
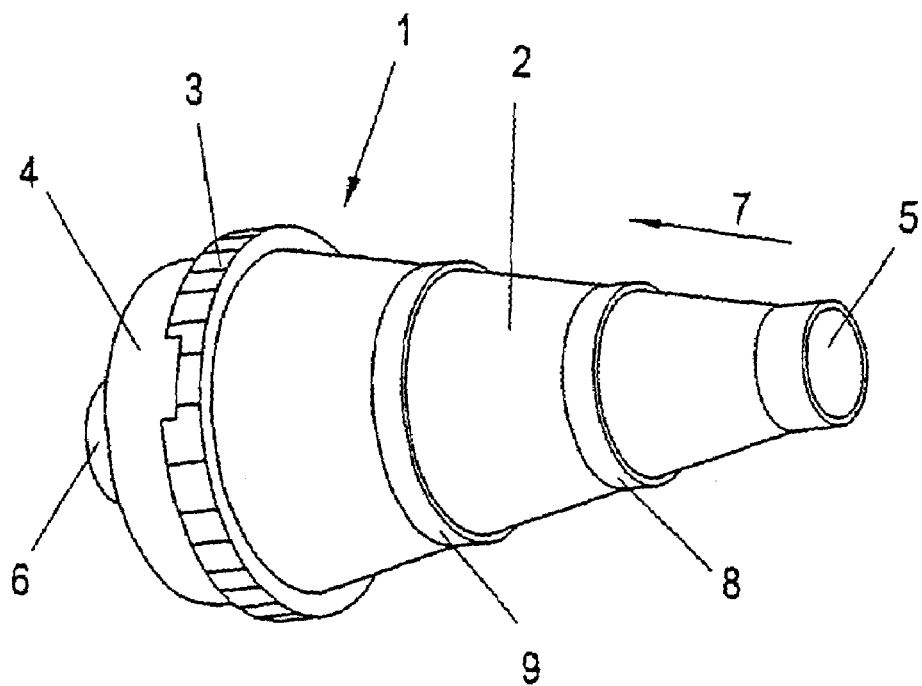
FIG. 1 is a perspective view of the inhalation aid according to the invention in an extracted operating position.
Figure 2:
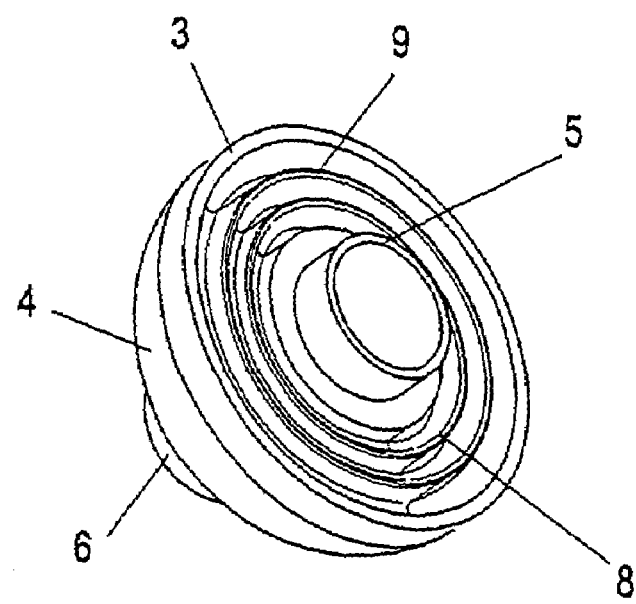
FIG. 2 is an illustration similar to that of FIG. 1, of the inhalation aid according to the invention in the retracted position or transport position.

From the position of use or application illustrated in FIG. 1, the expansion bellows 2 made of a continuous, elastic material, along arrow 7, can be brought into the folded position or transport position represented in FIG. 2, in which the inhalation aid 1 requires an accordingly reduced space.

The expansion bellows 2 is, for instance, made of silicone, wherein, in the embodiment illustrated, two ring-shaped reinforcements 8 and 9 are provided at a distance from each other along the extension of the conically tapering expansion bellows 2, which have different diameters or different clear widths in accordance with the conical taper of the expansion bellows 2 in the extracted state illustrated in FIG. 1.

As is apparent from FIG. 2, these ring-shaped reinforcements 8 and 9 in the folded state assume a mutually inserted or overlapping position, whereby also the opening 5 is defined by an appropriate reinforcement ring. In the folded state represented in FIG. 2, the material located between the reinforcement rings 8 and 9 is in a folded state in a predefined position so as to enable the position of use illustrated in FIG. 1 to be again assumed from the transport position illustrated in FIG. 2, by tensile action in the region of the opening 5.

If the expansion bellows 2 is designed to have different volumes, a modified number of reinforcements or elements 8, 9 may be provided in accordance with the shape of the expansion bellows 2.

From the exploded views according to FIGS. 3 and 4, it is apparent that the expansion bellows 2 on its end having the larger cross section is provided with a bead or flange 10, which is overlapped by a corresponding projection or flange 11 of the retaining ring 3, whereby, in FIG. 3, at a movement of the retaining ring 3 in the sense of arrow 12, the retaining ring is detached from the expansion bellows and, in particular, its bead or flange 10.

FIG. 4 schematically depicts the procedure of assembling the expansion bellows 2 including the attached retaining ring 3 with the pot-like housing 4 in the sense of arrow 13. The detachable connection between the retaining ring 3 and the housing 4 is, for instance, effected via a screw plug or a bayonet catch, wherein, to this end, the retaining ring is provided with appropriate recesses 14 and the housing is provided with complementary profiles 15, which will be more clearly apparent from FIGS. 5 and 6.

From the schematic illustrations according to FIGS. 5 and 6, it can be taken that the ring-shaped reinforcements 8 and 9 form a stepped region or step 16 on the outer surface of the expansion bellows 2. From the sectional illustration according to FIG. 6, it is further apparent that the ring-shaped reinforcements 8 and 9 have material cross sections that are enlarged relative to the immediately adjacent portions of the expansion bellows 2, wherein the expansion bellows 2, for simple folding from the position of use illustrated in FIG. 1 into the transport position represented in FIG. 2, may, moreover, be designed with an accordingly tapered cross section in the region following the ring-shaped reinforcements 8 and 9, to facilitate or support the folding procedure.

In the illustration according to FIGS. 5 and 6, appropriate recesses 15 are again indicated on the retaining ring 3, and adjusting or latch elements 16 are indicated on the housing 4, to form the desired locking mechanism or bayonet catch.

In addition, FIGS. 5 and 6 indicate an additional cover 17 for the opening 6 defining the mouthpiece, wherein a similar cover may also be provided on the opening 5 to prevent foreign matter from entering, for instance, in the transport position.

The simple detachability of the housing 4 from the retaining ring 3 as well as of the retaining ring 3 from the expansion bellows 2, as is indicated in FIGS. 3 and 4, enables the simple and proper cleaning of the interior of the chamber of the inhalation aid 1, which is defined by the expansion bellows 2, thus also allowing an accordingly simple and reliable assembly in a tight manner.

The invention claimed is

1. An inhalation aid for use in connection with an aerosol dispenser, said inhalation aid comprising
    a chamber having an opening at one end for connection to an aerosol dispenser and a mouthpiece opening at an opposite end of the chamber for drawing aerosol from the aerosol dispenser at the one end, said chamber having a variable volume and delimited or surrounded by a conically tapering expansion bellows made of a continuous, elastic material,
    the expansion bellows including at least one ring-shaped reinforcement having a material cross section increased relative to adjacent portions of the expansion bellows,
    a housing at the other end of the chamber, said housing including the mouthpiece opening, and
    a retaining ring removably connecting the housing to the expansion bellows at the other end of the chamber,
    the expansion bellows, in a folded state, being received in the housing,
    the retaining ring being connectable and detachably connectable with the housing provided to receive the expansion bellows.

2. The inhalation aid according to claim 1, wherein the expansion bellows is made of silicone.

3. The inhalation aid according to claim 1, wherein an outer surface of the expansion bellows is stepped or offset in a region of end faces of the at least one ring-shaped reinforcement oriented towards a tapering end.

4. The inhalation aid according to claim 1, wherein the expansion bellows has a reduced material cross section in a portion immediately following the at least one ring-shaped reinforcement, on a chamber side face oriented towards an interior of the expansion bellows.

5. The inhalation aid according to claim 1, wherein the expansion bellows, on the other end of the chamber has a bead or flange to which the retaining ring is fixable.

6. The inhalation aid according to claim 1, wherein the connection between the retaining ring and the housing is a screw connection or bayonet catch.

7. The inhalation aid according to claim 1, wherein a cover is provided for the openings of the chamber.

8. The inhalation aid according to claim 1, wherein the at least one ring-shaped reinforcement is of substantially constant diameter.

9. An inhalation aid for use in connection with an aerosol dispenser, said inhalation aid comprising
- a chamber having an opening at one end for connection to an aerosol dispenser and a mouthpiece opening at an opposite end of the chamber for drawing aerosol from the aerosol dispenser at the one end, said chamber having a variable volume and delimited or surrounded by a conically tapering expansion bellows made of a continuous, elastic material,
- the expansion bellows including at least one ring-shaped reinforcement having a material cross section increased relative to adjacent portions of the expansion bellows,
- a housing at the other end of the chamber, said housing including the mouthpiece opening,
- a retaining ring removably connecting the housing to the expansion bellows at the other end of the chamber,
- the expansion bellows, in a folded state, being received in the housing, and
- markings, or snap-on or adjusting elements being provided on at least one of the retaining ring and the housing.

10. The inhalation aid according to claim 9, wherein the expansion bellows is made of silicone.

11. The inhalation aid according to claim 9, wherein an outer surface of the expansion bellows is stepped or offset in a region of end faces of the at least one ring-shaped reinforcement oriented towards a tapering end.

12. The inhalation aid according to claim 9, wherein the expansion bellows has a reduced material cross section in a portion immediately following the at least one ring-shaped reinforcement, on a chamber side face oriented towards an interior of the expansion bellows.

13. The inhalation aid according to claim 9, wherein the expansion bellows, on the other end of the chamber has a bead or flange to which the retaining ring is fixable.

14. The inhalation aid according to claim 9, wherein a cover is provided for the openings of the chamber.

15. The inhalation aid according to claim 9, wherein the at least one ring-shaped reinforcement is of substantially constant diameter.

* * * * *